US 8,355,774 B2

(12) United States Patent
Markowitz et al.

(10) Patent No.: US 8,355,774 B2
(45) Date of Patent: Jan. 15, 2013

(54) SYSTEM AND METHOD TO EVALUATE ELECTRODE POSITION AND SPACING

(75) Inventors: H. Toby Markowitz, Roseville, MN (US); Shangqian Peter Zhang, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 260 days.

(21) Appl. No.: 12/609,734

(22) Filed: Oct. 30, 2009

(65) Prior Publication Data

US 2011/0106203 A1 May 5, 2011

(51) Int. Cl.
*A61B 5/05* (2006.01)
*A61B 19/00* (2006.01)
*A61N 1/00* (2006.01)

(52) U.S. Cl. ............... 600/424; 607/2; 607/27; 600/547; 128/899

(58) Field of Classification Search ................. 607/2, 27; 128/899; 600/424, 547
See application file for complete search history.

(56) References Cited

U.S. PATENT DOCUMENTS

| | | |
|---|---|---|
| 3,837,347 A | 9/1974 | Tower |
| 3,995,623 A | 12/1976 | Blake et al. |
| 4,506,680 A | 3/1985 | Stokes |
| 4,619,246 A | 10/1986 | Molgaard-Nielsen et al. |
| 4,649,924 A | 3/1987 | Taccardi |
| 4,696,304 A | 9/1987 | Chin |
| 4,801,297 A | 1/1989 | Mueller |
| 4,852,580 A | 8/1989 | Wood |
| 5,035,246 A | 7/1991 | Heuvelmans et al. |
| 5,076,285 A | 12/1991 | Hess et al. |
| 5,078,714 A | 1/1992 | Katims |
| 5,099,845 A | 3/1992 | Besz et al. |
| 5,167,239 A | 12/1992 | Cohen et al. |
| 5,255,680 A | 10/1993 | Darrow et al. |
| 5,265,622 A | 11/1993 | Barbere |
| 5,297,549 A | 3/1994 | Beatty et al. |
| 5,342,295 A | 8/1994 | Imran |
| 5,385,148 A | 1/1995 | Lesh et al. |
| 5,391,199 A | 2/1995 | Ben-Haim |
| 5,443,489 A | 8/1995 | Ben-Haim |

(Continued)

FOREIGN PATENT DOCUMENTS

EP 363117 4/1990

(Continued)

OTHER PUBLICATIONS

"EnSite NavX™ Navigation & Visualization Technology." 3 pages, St. Jude Medical. http://www.sjmprofessional.com/Products/US/Mapping-and-Visualization/EnSite-NavX-Navigation-and-Visualization-Technology.aspx Web. Accessed Jun. 19, 2009.

(Continued)

*Primary Examiner* — Niketa Patel
*Assistant Examiner* — William Levicky
(74) *Attorney, Agent, or Firm* — Harness, Dickey

(57) ABSTRACT

A method and apparatus for tracking and illustrating the location of leads positioned within the volume is disclosed. For example, the lead electrodes can be positioned within a heart of a patient that can be tracked over time. The lead electrodes can be tracked with an electrode potential or bio-impedance tracking system to determine the position of the lead electrodes. A method and apparatus is disclosed to analyze the position information for analyzing the selected position of the lead electrodes.

25 Claims, 6 Drawing Sheets

U.S. PATENT DOCUMENTS

| | | | |
|---|---|---|---|
| 5,480,422 A | 1/1996 | Ben-Haim | |
| 5,512,920 A | 4/1996 | Gibson | |
| 5,522,874 A | 6/1996 | Gates | |
| 5,546,951 A | 8/1996 | Ben-Haim | |
| 5,558,091 A | 9/1996 | Acker et al. | |
| 5,568,809 A | 10/1996 | Ben-haim | |
| 5,639,276 A | 6/1997 | Weinstock et al. | |
| 5,697,377 A | 12/1997 | Wittkampf | |
| 5,713,946 A | 2/1998 | Ben-Haim | |
| 5,797,849 A | 8/1998 | Vesely et al. | |
| 5,800,407 A | 9/1998 | Eldor et al. | |
| 5,840,025 A | 11/1998 | Ben-Haim | |
| 5,916,193 A | 6/1999 | Stevens et al. | |
| 5,944,022 A * | 8/1999 | Nardella et al. | 128/899 |
| 5,983,126 A | 11/1999 | Wittkampf | |
| 6,009,349 A | 12/1999 | Mouchawar et al. | |
| 6,050,267 A | 4/2000 | Nardella et al. | |
| 6,088,527 A | 7/2000 | Rybczynski | |
| 6,090,105 A | 7/2000 | Zepeda et al. | |
| 6,122,552 A | 9/2000 | Tockman et al. | |
| 6,152,946 A | 11/2000 | Broome et al. | |
| 6,196,230 B1 | 3/2001 | Hall et al. | |
| 6,226,547 B1 | 5/2001 | Lockhart et al. | |
| 6,236,886 B1 | 5/2001 | Cherepenin et al. | |
| 6,240,307 B1 | 5/2001 | Beatty et al. | |
| 6,246,468 B1 | 6/2001 | Dimsdale | |
| 6,256,121 B1 | 7/2001 | Lizotte et al. | |
| 6,301,498 B1 | 10/2001 | Greenberg et al. | |
| 6,330,356 B1 | 12/2001 | Sundareswaran et al. | |
| 6,389,187 B1 | 5/2002 | Greenaway et al. | |
| 6,470,205 B2 | 10/2002 | Bosselmann et al. | |
| 6,490,474 B1 | 12/2002 | Willis et al. | |
| 6,527,782 B2 | 3/2003 | Hogg et al. | |
| 6,546,270 B1 | 4/2003 | Goldin et al. | |
| 6,569,160 B1 | 5/2003 | Goldin et al. | |
| 6,574,498 B1 | 6/2003 | Gilboa | |
| 6,595,989 B1 | 7/2003 | Schaer | |
| 6,602,271 B2 | 8/2003 | Adams et al. | |
| 6,611,141 B1 | 8/2003 | Schulz et al. | |
| 6,701,176 B1 | 3/2004 | Halperin et al. | |
| 6,714,806 B2 | 3/2004 | Iaizzo et al. | |
| 6,771,996 B2 | 8/2004 | Bowe et al. | |
| 6,868,195 B2 | 3/2005 | Fujita et al. | |
| 6,888,623 B2 | 5/2005 | Clements | |
| 6,892,091 B1 | 5/2005 | Ben-Haim et al. | |
| 6,898,302 B1 | 5/2005 | Brummer | |
| 6,990,370 B1 | 1/2006 | Beatty et al. | |
| 7,020,522 B1 | 3/2006 | Hoijer et al. | |
| 7,047,073 B2 | 5/2006 | Hoijer et al. | |
| 7,189,208 B1 | 3/2007 | Beatty et al. | |
| 7,207,989 B2 | 4/2007 | Pike, Jr. et al. | |
| 7,215,430 B2 | 5/2007 | Kacyra et al. | |
| 7,263,397 B2 | 8/2007 | Hauck et al. | |
| 7,305,121 B2 | 12/2007 | Kaufmann et al. | |
| 7,328,071 B1 | 2/2008 | Stehr et al. | |
| 7,369,901 B1 | 5/2008 | Morgan et al. | |
| 7,421,300 B2 | 9/2008 | Smits et al. | |
| 7,479,141 B2 | 1/2009 | Kleen et al. | |
| 7,529,584 B2 | 5/2009 | Laske et al. | |
| 7,686,757 B2 | 3/2010 | Minai | |
| 7,715,604 B2 | 5/2010 | Sun et al. | |
| 7,824,328 B2 | 11/2010 | Gattani et al. | |
| 7,848,787 B2 | 12/2010 | Osadchy | |
| 7,941,213 B2 | 5/2011 | Markowitz et al. | |
| 7,988,639 B2 | 8/2011 | Starks | |
| 8,106,905 B2 | 1/2012 | Markowitz et al. | |
| 8,135,467 B2 | 3/2012 | Markowitz et al. | |
| 8,175,681 B2 | 5/2012 | Hartmann et al. | |
| 8,185,192 B2 | 5/2012 | Markowitz et al. | |
| 8,208,991 B2 | 6/2012 | Markowitz et al. | |
| 8,214,018 B2 | 7/2012 | Markowitz et al. | |
| 2001/0000800 A1 | 5/2001 | Partridge et al. | |
| 2001/0031920 A1 | 10/2001 | Kaufman et al. | |
| 2002/0045810 A1 | 4/2002 | Ben-Haim | |
| 2002/0049375 A1 | 4/2002 | Strommer et al. | |
| 2002/0077544 A1 | 6/2002 | Shahidi | |
| 2002/0111662 A1 | 8/2002 | Iaizzo et al. | |
| 2002/0147488 A1 | 10/2002 | Doan et al. | |
| 2002/0183817 A1 | 12/2002 | Van Venrooij et al. | |
| 2003/0028118 A1 | 2/2003 | Dupree et al. | |
| 2003/0055324 A1 | 3/2003 | Wasserman | |
| 2003/0078494 A1 | 4/2003 | Panescu et al. | |
| 2003/0108853 A1 | 6/2003 | Chosack et al. | |
| 2003/0114908 A1 | 6/2003 | Flach | |
| 2003/0225434 A1 | 12/2003 | Glantz et al. | |
| 2003/0231789 A1 | 12/2003 | Willis et al. | |
| 2004/0001075 A1 | 1/2004 | Balakrishnan et al. | |
| 2004/0019359 A1 | 1/2004 | Worley et al. | |
| 2004/0044295 A1 | 3/2004 | Reinert et al. | |
| 2004/0064159 A1 | 4/2004 | Hoijer et al. | |
| 2004/0068312 A1 | 4/2004 | Sigg et al. | |
| 2004/0070582 A1 | 4/2004 | Smith et al. | |
| 2004/0097805 A1 | 5/2004 | Verard et al. | |
| 2004/0097806 A1 | 5/2004 | Hunter et al. | |
| 2004/0162599 A1 | 8/2004 | Kurth | |
| 2004/0215298 A1 | 10/2004 | Richardson et al. | |
| 2004/0228453 A1 | 11/2004 | Dobbs et al. | |
| 2004/0236395 A1 | 11/2004 | Iaizzo et al. | |
| 2004/0249281 A1 | 12/2004 | Olstad | |
| 2004/0249430 A1 | 12/2004 | Martinez et al. | |
| 2004/0254437 A1 | 12/2004 | Hauck et al. | |
| 2005/0004476 A1 | 1/2005 | Payvar et al. | |
| 2005/0018888 A1 | 1/2005 | Zonneveld | |
| 2005/0119550 A1 | 6/2005 | Serra et al. | |
| 2005/0177151 A1 | 8/2005 | Coen et al. | |
| 2005/0187432 A1 | 8/2005 | Hale et al. | |
| 2005/0245803 A1 | 11/2005 | Glenn, Jr. et al. | |
| 2006/0013523 A1 | 1/2006 | Childlers et al. | |
| 2006/0058604 A1 | 3/2006 | Avinash et al. | |
| 2006/0116576 A1 | 6/2006 | McGee et al. | |
| 2006/0117773 A1 | 6/2006 | Street et al. | |
| 2006/0135883 A1 | 6/2006 | Jonsson et al. | |
| 2006/0153468 A1 | 7/2006 | Solf et al. | |
| 2006/0173268 A1 | 8/2006 | Mullick et al. | |
| 2006/0173381 A1 | 8/2006 | Eck | |
| 2006/0200049 A1 | 9/2006 | Leo et al. | |
| 2006/0206157 A1 | 9/2006 | Hoijer | |
| 2006/0229513 A1 | 10/2006 | Wakai | |
| 2006/0229594 A1 | 10/2006 | Francischelli et al. | |
| 2006/0247520 A1 | 11/2006 | McGee | |
| 2006/0253116 A1 | 11/2006 | Avitall et al. | |
| 2007/0016084 A1 | 1/2007 | Denault | |
| 2007/0038052 A1 | 2/2007 | Swoyer et al. | |
| 2007/0043413 A1 | 2/2007 | Eversull et al. | |
| 2007/0046661 A1 | 3/2007 | Ma et al. | |
| 2007/0049817 A1 | 3/2007 | Preiss et al. | |
| 2007/0066889 A1 | 3/2007 | Boese et al. | |
| 2007/0112388 A1 | 5/2007 | Salo | |
| 2007/0123944 A1 | 5/2007 | Zdeblick | |
| 2007/0135721 A1 | 6/2007 | Zdeblick | |
| 2007/0135803 A1 | 6/2007 | Belson | |
| 2007/0156019 A1 | 7/2007 | Larkin et al. | |
| 2007/0164900 A1 | 7/2007 | Schneider et al. | |
| 2007/0167801 A1 | 7/2007 | Webler et al. | |
| 2007/0232898 A1 | 10/2007 | Huynh et al. | |
| 2007/0252074 A1 | 11/2007 | Ng et al. | |
| 2007/0270682 A1 | 11/2007 | Huang et al. | |
| 2007/0299351 A1 | 12/2007 | Harlev et al. | |
| 2007/0299352 A1 | 12/2007 | Harlev et al. | |
| 2007/0299353 A1 | 12/2007 | Harlev et al. | |
| 2008/0015466 A1 | 1/2008 | Lerman | |
| 2008/0024493 A1 | 1/2008 | Bordoloi et al. | |
| 2008/0038197 A1 | 2/2008 | John et al. | |
| 2008/0058656 A1 | 3/2008 | Costello et al. | |
| 2008/0071142 A1 | 3/2008 | Gattani et al. | |
| 2008/0118117 A1 | 5/2008 | Gauldie et al. | |
| 2008/0123910 A1 | 5/2008 | Zhu | |
| 2008/0132800 A1 | 6/2008 | Hettrick et al. | |
| 2008/0183072 A1 | 7/2008 | Robertson et al. | |
| 2008/0207997 A1 | 8/2008 | Higgins et al. | |
| 2008/0221425 A1 | 9/2008 | Olson et al. | |
| 2008/0221438 A1 | 9/2008 | Chen et al. | |
| 2008/0243025 A1 | 10/2008 | Holmstrom et al. | |
| 2008/0249375 A1 * | 10/2008 | Obel | 600/301 |
| 2008/0255470 A1 | 10/2008 | Hauck et al. | |
| 2009/0017430 A1 | 1/2009 | Muller-Daniels et al. | |
| 2009/0063118 A1 | 3/2009 | Dachille et al. | |

| | | | |
|---|---|---|---|
| 2009/0093857 A1 | 4/2009 | Markowitz et al. | |
| 2009/0099619 A1 | 4/2009 | Lessmeier et al. | |
| 2009/0103793 A1 | 4/2009 | Borland et al. | |
| 2009/0126575 A1 | 5/2009 | Son et al. | |
| 2009/0129477 A1 | 5/2009 | Yang | |
| 2009/0131955 A1 | 5/2009 | Wenderow et al. | |
| 2009/0192381 A1 | 7/2009 | Brockway et al. | |
| 2009/0211909 A1 | 8/2009 | Nesbitt | |
| 2009/0227861 A1 | 9/2009 | Ganatra et al. | |
| 2009/0253976 A1 | 10/2009 | Harlev et al. | |
| 2009/0253985 A1 | 10/2009 | Shachar et al. | |
| 2009/0262109 A1 | 10/2009 | Markowitz et al. | |
| 2009/0262979 A1 | 10/2009 | Markowitz et al. | |
| 2009/0262980 A1 | 10/2009 | Markowitz et al. | |
| 2009/0262982 A1 | 10/2009 | Markowitz et al. | |
| 2009/0262992 A1 | 10/2009 | Markowitz et al. | |
| 2009/0264727 A1 | 10/2009 | Markowitz et al. | |
| 2009/0264738 A1 | 10/2009 | Markowitz et al. | |
| 2009/0264739 A1 | 10/2009 | Markowitz et al. | |
| 2009/0264740 A1 | 10/2009 | Markowitz et al. | |
| 2009/0264741 A1 | 10/2009 | Markowitz et al. | |
| 2009/0264742 A1 | 10/2009 | Markowitz et al. | |
| 2009/0264743 A1 | 10/2009 | Markowitz et al. | |
| 2009/0264744 A1 | 10/2009 | Markowitz et al. | |
| 2009/0264745 A1 | 10/2009 | Markowitz et al. | |
| 2009/0264746 A1 | 10/2009 | Markowitz et al. | |
| 2009/0264747 A1 | 10/2009 | Markowitz et al. | |
| 2009/0264748 A1 | 10/2009 | Markowitz et al. | |
| 2009/0264749 A1 | 10/2009 | Markowitz et al. | |
| 2009/0264750 A1 | 10/2009 | Markowitz et al. | |
| 2009/0264751 A1 | 10/2009 | Markowitz et al. | |
| 2009/0264752 A1 | 10/2009 | Markowitz et al. | |
| 2009/0264777 A1 | 10/2009 | Markowitz et al. | |
| 2009/0264778 A1 | 10/2009 | Markowitz et al. | |
| 2009/0265128 A1 | 10/2009 | Markowitz et al. | |
| 2009/0267773 A1 | 10/2009 | Markowitz et al. | |
| 2009/0297001 A1 | 12/2009 | Markowitz et al. | |
| 2009/0306732 A1* | 12/2009 | Rosenberg et al. | 607/9 |
| 2010/0004724 A1 | 1/2010 | Markowitz et al. | |
| 2010/0030298 A1 | 2/2010 | Martens et al. | |
| 2010/0152571 A1 | 6/2010 | Hartmann et al. | |
| 2011/0054304 A1 | 3/2011 | Markowitz et al. | |
| 2012/0123474 A1 | 5/2012 | Zajac et al. | |
| 2012/0123541 A1 | 5/2012 | Albertorio et al. | |
| 2012/0130232 A1 | 5/2012 | Markowitz et al. | |

FOREIGN PATENT DOCUMENTS

| | | |
|---|---|---|
| EP | 1393674 A1 | 3/2004 |
| EP | 1421913 A1 | 5/2004 |
| EP | 2136706 | 12/2009 |
| WO | WO-9848722 A1 | 11/1998 |
| WO | WO-0134050 A2 | 5/2001 |
| WO | WO-02064040 A2 | 8/2002 |
| WO | WO-2005112836 A2 | 12/2005 |
| WO | WO-2006042039 A2 | 4/2006 |
| WO | WO-2006117773 A1 | 11/2006 |
| WO | WO-2007067945 | 6/2007 |
| WO | WO-2007111542 A1 | 10/2007 |
| WO | WO-2007136451 A2 | 11/2007 |
| WO | WO-2008108901 | 9/2008 |
| WO | WO-2008147961 A1 | 12/2008 |
| WO | WO-2009126575 A1 | 10/2009 |
| WO | WO-2009129471 A1 | 10/2009 |
| WO | WO-2010074986 A1 | 7/2010 |

OTHER PUBLICATIONS

"Local Lisa® Intracardiac Navigation System Model 9670000/9670025." Technical Manual Version 1.2, Chapter 1, pp. 1-19. 2004.
Brenner, David J., Ph.D., "Computed Tomography—An Increasing Source of Radiation Exposure", The New England Journal of Medicine (Nov. 29, 2007), pp. 2277-2284.
Gepstein, Lior, M.D., "A Novel Method for Nonfluoroscopic Catheter-Based Electroanatomical Mapping of the Heart, In Vitro and In Vivo Accuracy Results", American Heart Association, Learn and Live, Circulation (1997), http://circ.ahajournals.org/cgi/content/abstract/95/6/1611 printed Oct. 2, 2008.
International Preliminary Report on Patentability and Written Opinion for PCT/US2009/040998 mailed Oct. 28, 2010, 2009 claiming benefit of U.S. Appl. No. 12/421,332, filed Apr. 9, 2009; which claims priority to U.S. Appl. No. 61/105,957, filed Oct. 16, 2008; U.S. Appl. No. 12/117,549, filed May 8, 2008.
International Preliminary Report on Patentability and Written Opinion for PCT/US2009/0400984 mailed Oct. 28, 2010, claiming benefit of U.S. Appl. No. 12/117,549, filed May 8, 2008.
International Preliminary Report on Patentability and Written Opinion for PCT/US2009/040979 mailed Oct. 28, 2010 claiming benefit of U.S. Appl. No. 12/117,537, filed May 8, 2008.
International Preliminary Report on Patentability and Written Opinion mailed Oct. 29, 2009 for PCT/US2007/089087, of which U.S. Appl. No. 12/492,906, filed Jun. 26, 2009 claims benefit.
International Search Report and Written Opinion for PCT/US2008/088189 mailed Apr. 3, 2009, claiming benefit of U.S. Appl. No. 12/183,796, filed Jul. 31, 2008; and claims priority to U.S. Appl. No. 11/966,382, filed Dec. 28, 2007.
International Search Report and Written Opinion for PCT/US2009/0400984 mailed Sep. 21, 2009, claiming benefit of U.S. Appl. No. 12/117,549, filed May 8, 2008.
International Search Report and Written Opinion for PCT/US2009/040998 mailed Jul. 29, 2009 claiming benefit of U.S. Appl. No. 12/421,332, filed Apr. 9, 2009; which claims priority to U.S. Appl. No. 61/105,957, filed Oct. 16, 2008; U.S. Appl. No. 12/117,549, filed May 8, 2008.
International Search Report and Written Opinion for PCT/US2009/067486 mailed May 4, 2010, claiming benefit of U.S. Appl. No. 12/336,085, filed Dec. 16, 2008.
International Search Report and Written Opinion mailed Dec. 6, 2010 for PCT/US2010/051248, which claims benefit of U.S. Appl. No. 12/609,734, filed Oct. 30, 2009.
International Search Report and Written Opinon for PCT/US2009/040979 mailed Sep. 21, 2009 claiming benefit of U.S. Appl. No. 12/117,537, filed May 8, 2008.
International Search Report for PCT/US2007/089087 mailed Jul. 9, 2008, of which U.S. Appl. No. 12/492,906, filed Jun. 26, 2009 claims benefit.
Invitation to Pay Additional Fees for PCT/US2009/0400984 mailed Jul. 30, 2009, claiming benefit of U.S. Appl. No. 12/117,549, filed May 8, 2008.
Invitation to Pay Additional Fees for PCT/US2009/040979 mailed Jul. 30, 2009 claiming benefit of U.S. Appl. No. 12/117,537, filed May 8, 2008.
Invitation to Pay Additional Fees for PCT/US2009/067486 mailed Mar. 5, 2010, claiming benefit of U.S. Appl. No. 12/336,085, filed Dec. 16, 2008.
Invitation to Pay Additional Fees for PCT/US2010/047241 mailed Jan. 10, 2011, claiming benefit of U.S. Appl. No. 12/844,065, filed Jul. 27, 2010.
Jiang, Yuan. "An Impedance-Based Catheter Poisitioning System for Cardiac Mapping and Navigation." IEEE Transactions on Biomedical Engineering, (Aug. 2009) pp. 1963-1970, vol. 56, No. 8.
Markowitz, Toby, et al., "Unleaded: The Fluoroless 3D Lead Implant", Presented at Heart Rhythm Society, Denver, CO, (May 2007) 1 pg.
Markowitz, Toby, et al., Abstract Submission, "Unleaded: "The Fluoroless 3D Lead Implant, Mar. 2007 2 pgs.
Milstein, S. et al., "Initial Clinical Results of Non-Fluoroscopic Pacemaker Lead Implantation." (pre-presentation abstract) May 14-17, 2008. 2 pgs.
Milstein, S. et al., "Initial Clinical Results of Non-Fluoroscopic Pacemaker Lead Implantation." (poster presentation) May 14-17, 2008. 1 pg.
Nelder, J.A., et al. "A simplex method for function minimization." vol. 7, Issue 4, (1965) pp. 308-313.The Computer Journal.
Savage, George, M.D., "Electric Tomography (ET)—A Novel Method for Assessing Myocardial Motion and Cardiac Performance", Heart Rhythm Society, Denver, CO (May 9-12, 2007) 1 pg.
Wittkampf, Fred, H.M., et al., "LocaLisa: New Technique for Real-Time 3-Dimensional Localization of Regular Intracardiac Electrodes." Circulation Journal of the American Heart Association, 1999; 99; 13-12-1317.

Wittkampf, Fred., H.M., et al. "Accuracy of the LocaLisa System in Catheter Ablation Procedures." Journal of Electrocardiology vol. 32 Supplement (1999). Heart Lung Institute, University Hospital Utrecht, The Netherlands.

Birkfellner, Wolfgang, et al. "Calibration of Tracking Systems in a Surgical Environment," IEEE Transactions on Medical Imaginge, IEEE Service Center, Piscataway, NJ, US, vol. 17, No. 5. (Oct. 1, 1998) XP011035767. ISSN: 0278-0062 the whole document.

Hubert-Tremblay, Vincent, et al. "Octree indexing of DICOM images for voxel number reduction and improvement of Monte Carolo simulation computing efficiency," Medical Physics, AIP, Melville, NY, US, vol. 33, No. 8, (Jul. 21, 2006) pp. 2819-2831, XP012092212, ISSN: 0094-2405, DOI: 10.1118/1.2214305 pp. 2820-2821.

International Preliminary Report on Patentability mailed Oct. 11, 2011 for PCT/US2010/030534 claming benefit of U.S. Appl. No. 12/421,375, filed Apr. 9, 2009.

International Search Report and Written Opinon mailed Jul. 25, 2011 for PCT/US2010/047241 claiming benefit of U.S. Appl. No. 12/844,065, filed Jul. 27, 2010.

International Search Report mailed Sep. 13, 2010 for PCT/US2010/030534 claming benefit of U.S. Appl. No. 12/421,375, filed Apr. 9, 2009.

Invitation to Pay Additional Fees mailed Jul. 7, 2010 for PCT/US2010/030534 claiming benefit of U.S. Appl. No. 12/421,375, filed Apr. 9, 2009.

China Office Action for Chinese Application No. 20980121281.3 (PCT/US2009/040998) published as Chinese Publication No. 201250800705320 issued on May 11, 2012 claiming benefit of U.S. Appl. No. 12/425,480, filed Apr. 17, 2009.

International Preliminary Report on Patentability and Written Opinion for PCT/US2010/047241 mailed Mar. 15, 2012 claiming benefit of U.S. Appl. No. 12/844,065, filed Jul. 27, 2010.

* cited by examiner

SYSTEM AND METHOD TO EVALUATE ELECTRODE POSITION AND SPACING

FIELD

The subject disclosure is related to measuring distances and a subject, and particularly to measuring anatomical distances in a heart.

BACKGROUND

This section provides background information related to the present disclosure which is not necessarily prior art.

During a selected procedure, such as a cardiac resynchronization therapy (CRT) implants are positioned within a subject, such as in the heart of the subject. Particularly, in a CRT procedure in a human, a lead that can be used for pacing can be implanted in both a right ventricle and a left ventricle of the patient's heart. However, the exact position of the leads in the right and left ventricles can vary for achieving a selected result with the CRT implant. Additionally, stimulation can be applied to the selected leads according to different parameters to achieve a selected result.

SUMMARY

This section provides a general summary of the disclosure, and is not a comprehensive disclosure of its full scope or all of its features.

When positioning implant leads in the heart, for example, during an implantation procedure for CRT, the leads can be positioned in the heart, at least initially, in a partially removeable manner. For example, as the leads are positioned in the heart, they can include a screw-in lead tip that can be screwed in and then extracted from the tissue to allow repositioning prior to the completion of a procedure. During the procedure, the leads can be used to stimulate the hearts at a selected initial implantation location to determine whether appropriate resynchronization is occurring. In particular, the procedure is conducted to obtain synchrony between the right ventricle and the left ventricle. Various information can be collected to determine whether synchrony is occurring. Information can include the position of the lead tips as surrogates of heat wall position and those positions over time used to estimate or to determine wall motion or volume of ejection of blood from the heart.

Leads can be positioned in the heart of the subject and a tracking system, such as an electro-potential or position sensing unit tracking system can be used to determine the location of the leads over time to estimate or confirm synchrony within the heart. For example, the Local Lisa® sold by Medtronic, Inc. can be used to determine the location of the leads, as discussed further herein. In addition, various other systems can be used, as discussed herein, to identify or measure movement of leads and determine anatomical motions or synchrony, as discussed herein.

According to various embodiments, a method of determining movement of a portion of a subject includes positioning a first implantable lead having a first implantable electrode into a structure of the subject and positioning the first implantable electrode at a first location and positioning a second implantable lead having a second implantable electrode into a structure of the subject and positioning the second implantable electrode at a second location. A third electrode can also be positioned on or in the subject. At least two axes of current can be injected into a volume of the subject and a first impedance using the positioned first implantable electrode and the third electrode and a second impedance using the positioned second implantable electrode and the third electrode can be determined. Instructions can be executed with a processor external to the subject to determine a plurality of sequential first positions of the first implantable electrode and a plurality of sequential second positions of the second implantable electrode based on the determined first impedance and the determined second impedance using the positioned first implantable electrode, the positioned second implantable electrode, and the third electrode. Also, motion of the structure of the subject based on the determined plurality of sequential first positions of the first implantable electrode and the plurality of sequential second positions of the second implantable electrode can be determined.

According to various embodiments, a method of determining movement of a portion of a subject includes positioning a first implantable lead having a first implantable electrode into a right heart portion of the subject and positioning the first implantable electrode at a first location in the right heart portion and positioning a second implantable lead having a second implantable electrode into a left heart portion of the subject and positioning the second implantable electrode at a second location in the left heart portion. First pacing parameters can be selected and the heart of the subject can be paced according to the selected first pacing parameters with the first implantable electrode and the second implantable electrode. Tracking, relative to a reference portion, the location of the first implantable electrode in the right heart portion and the second implantable electrode in the left heart portion with an external tracking system can be performed and instructions can be executed with a processor external to the subject to determine a plurality of sequential first positions of the first implantable electrode and a plurality of sequential second positions of the second implantable electrode based on the determined impedance using both the positioned first implantable electrode and the positioned second implantable electrode. The plurality of first sequential positions and the plurality of second sequential positions can be projected onto a selected plane of the subject. Also, a determination of whether synchrony of the heart of the subject exists based on the projected plurality of first sequential positions and plurality of second sequential positions can be made.

According to various embodiments, a system to determine motion of a structure in a subject having a first lead electrode operable to be implanted and connected to an implantable medical device, a second lead electrode operable to be implanted and connected to the implantable medical device, and at least two pair of axis electrodes operable to inject two axes of current into the subject is disclosed. The system can include a processor operable to execute instructions. The instructions can include determining a position of the first electrode and the second electrode based on a determined impedance with the first electrode and the second electrode, projecting the determined positions of the first electrode and the second electrode onto a selected unit vector; and determining a trend of positions over time of the first electrode and the second electrode for illustration relative to the selected unit vector. The system can also include a display device to display the determined trend of positions on the selected unit vector over time including a first icon representing a trace of positions of the first electrode over time and a second icon representing a trace of positions of the second electrode over time.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Overview

Figure 1:
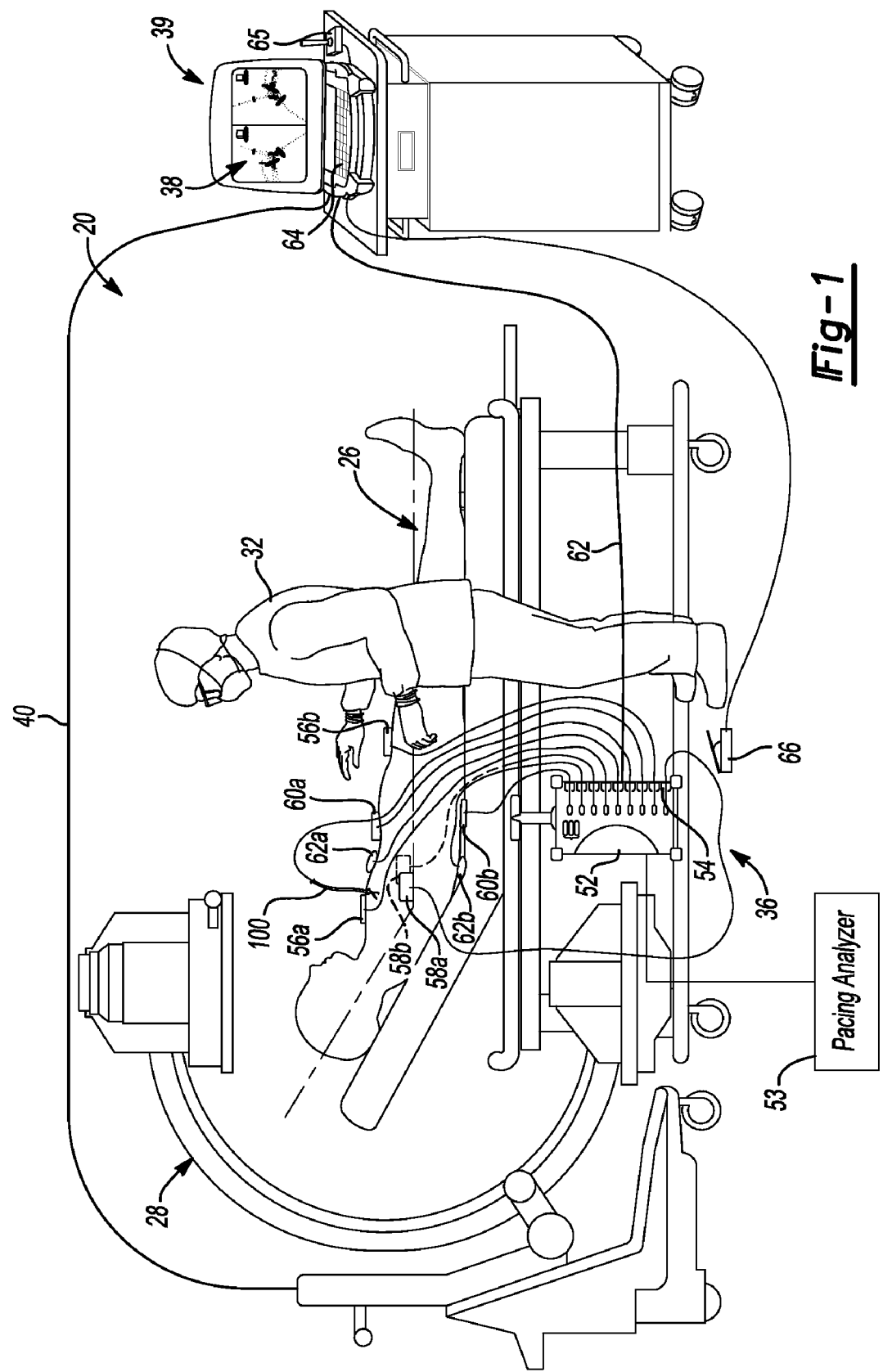
FIG. 1 is a schematic drawing of an exemplarily operating theater.

As discussed herein, a navigation system, such as the navigation system 20 illustrated in FIG. 1, can be used to navigate a procedure relative to a patient 26. As discussed in detail herein, various instruments can be moved relative to the patient 26 and tracked relative to the patient 26. Although an image-guided system can include acquiring image data of the patient 26, such as with an imaging device 28, the imaging device is not required. Rather, locations of various electrodes can be determined for various purposes. Exemplary locating or tracking systems to determine the position of leads over time can also include electro-potential systems including those disclosed in U.S. patent application Ser. No. 12/421,364, filed on Apr. 9, 2009, incorporated herein by reference.

According to various embodiments, a portion of the patient's 26 anatomy can be mapped by identifying a plurality of points within the patient 26 by determining a relative location of an instrument. The plurality of points can be illustrated individually, or sequentially, or a surface can be illustrated over or without the plurality of points to illustrate or identify a portion of the anatomy of the patient 26. This mapping is not required, however, for viewing or analyzing electrode movement in the patient 26. If a map is created of the patient 26 or a portion of the patient 26, either with or without a surface rendered relative to the individual points, a procedure can be guided or navigated using the map data. Other image data can also be acquired of the patient 26, such as with a fluoroscopic system, magnetic resonance imaging (MRI) System, computed tomography (CT) Imaging System, three-dimensional echo, ultrasound (2D, 3D, or 4D), or other imaging systems such as the imaging system 28.

Figure 2:
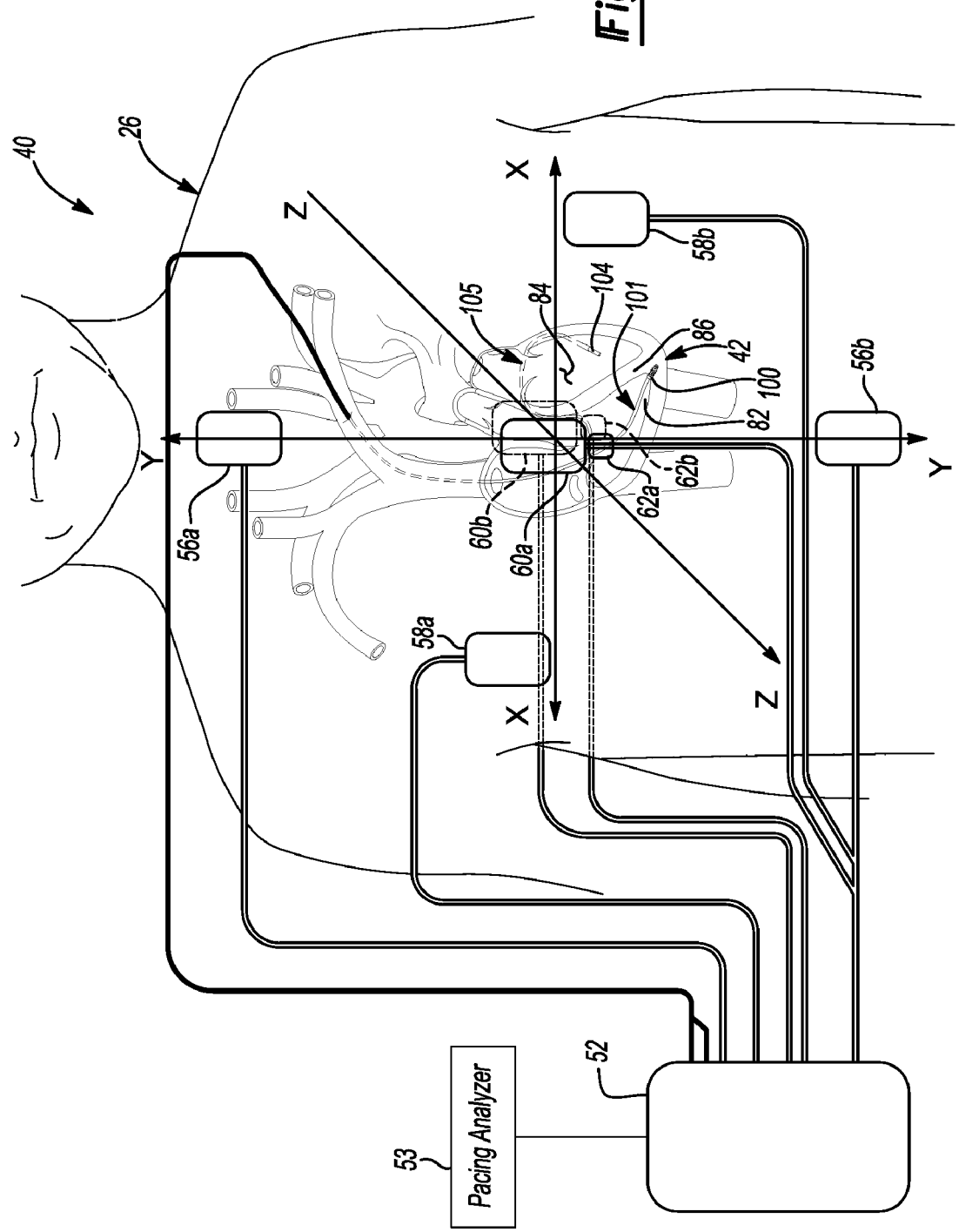
FIG. 2 is a detailed view of an electro-potential tracking system associated with a volume.
Figure 3:
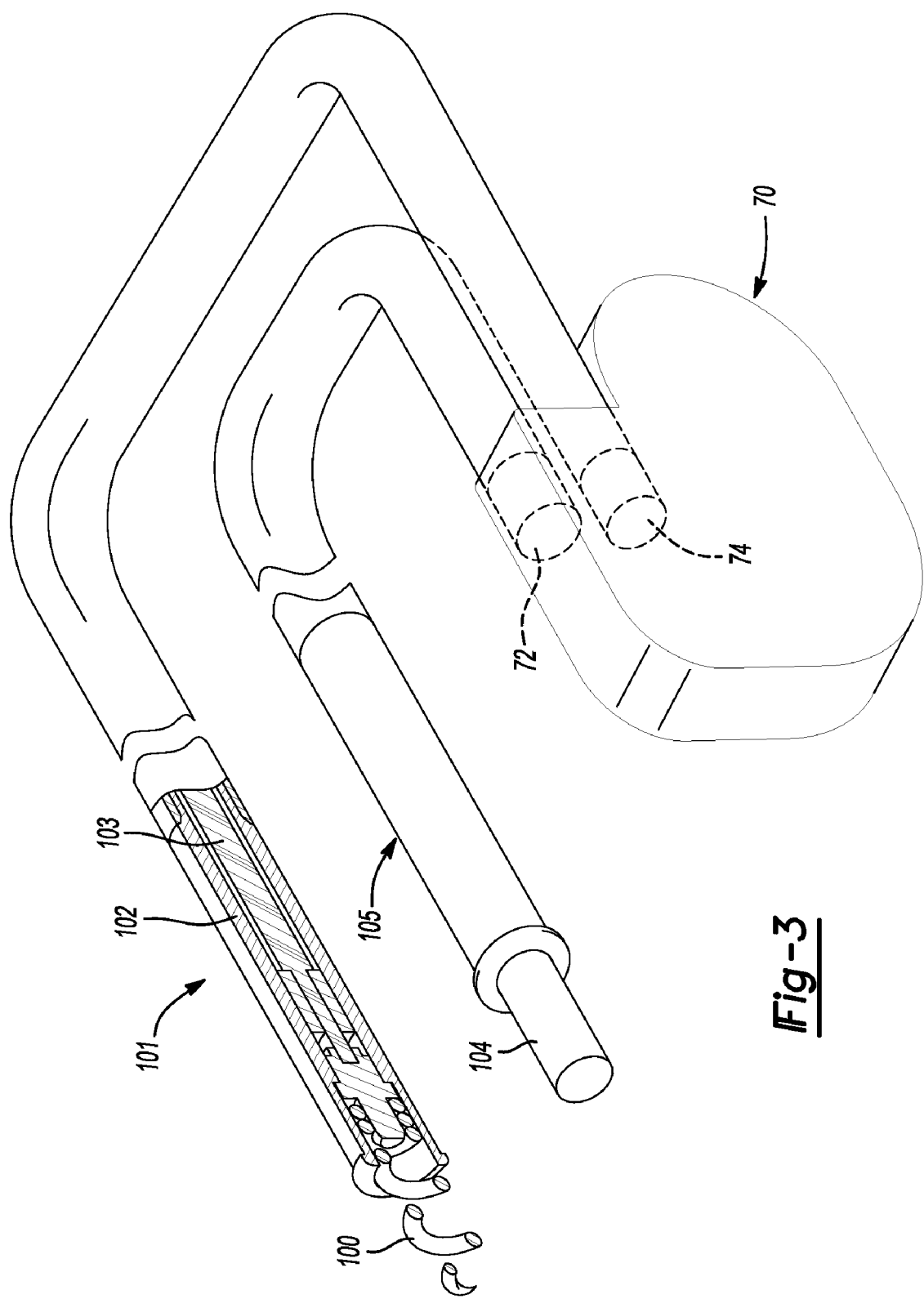
FIG. 3 is a cross-sectional detailed view of a lead electrode.

With reference to FIGS. 1 and 2, the navigation or mapping system 20 can be operated by a user 32 with an instrument (including the lead 101 in FIG. 3). The instrument can be navigated relative to the patient 26. The instrument can be moved relative to the patient 26 for various procedures, including lead (e.g. temporary or permanent implantable cardiac pacing leads, with insulated wiring for stimulating and/or recording signals in or on the heart) placement relative to a heart 42, mapping of the heart 42, mapping of a selected organ of the patient 26, or guiding or navigating the instrument relative to any appropriate portion of the patient 26.

The navigation system 20 can include various components, such as the optional imaging device 28. The optional imaging device 28 can include a fluoroscope, such as a fluoroscope configured as a C-arm. The display device 38 can be a part of a processor or processor system, such as a workstation 39. Images acquired with the imaging device 28 can be displayed on a display device 38 that is associated with the imaging device 28 via a communication system 40, such as a cable. In addition, if the imaging device is an x-ray imaging device any radio-opaque portions will appear as a part of the image when viewed, including the instrument. Further, other imaging systems, such as ultrasound, can be used to image the patient 26 and may also include information regarding instruments within the imaging field of the ultrasound transducer.

The navigation system 20 can further include a Position Sensing Unit (PSU) 36 as illustrated in FIG. 2. The PSU 36 can include an impedance or Electrical Potential (EP) system. The PSU can be the LocaLisa® Intracardiac Navigation System as previously provided by Medtronic, Inc. of Minneapolis, Minn., USA. The PSU 36 can also include any appropriate tracking system such as an electromagnetic (EM) or optical tracking system. An exemplary EM tracking system can include the Stealthstation® Axiem® electromagnetic tracking system and an exemplary optical tracking systems include the Stealthstation® TRIA® optical tracking system, both sold by Medtronic Navigation, Inc. having a place of business in Colorado, USA.

The PSU can also include or alternatively include an excitable wireless monitoring system as disclosed in U.S. patent application Ser. No. 11/565,283, filed on Nov. 30, 2006 (now published as U.S. Pat. App. Pub. No. 2008/0132800), incorporated herein by reference. In the excitable wireless monitoring system an excitable wireless marker can be positioned in the patient 26, such as being connected to or associated with a lead or lead electrode. The excitable wireless marker can be excited with an excitation signal and then wirelessly transmit a response signal. In an example, excitable wireless marker can receive an excitation signal at a selected resonant frequency to charge a capacitor. Once the excitation signal ceases, the excitable wireless marker can then transmit a response signal with the charge in the capacitor. The response signal can be used to determine location of the excitable wireless marker.

Bio-Impedance Position Sensing Unit

If the PSU 36 includes an EP tracking unit it can include a control or driving unit 52 that includes one or more input or output connectors 54 to interconnect with a plurality of current conducting or drive patches or electrodes connected directly with the patient 26. The current patches can include patches to create axes, such as three substantially orthogonal voltage or current axes, within the patient 26. For example, a first y-axis patch 56a and a second y-axis patch 56b can be interconnected with the patient 26 to form a y-axis (such as an axis that is generally superior-inferior of a patient as illustrated in FIG. 2) with a conductive path such that the conducted current establishes a voltage potential gradient substantially along this axis and between the patches 56a and 56b. A related y-axis current flows from the first y-axis patch 56a to the second y-axis patch 56b substantially along the y-axis. Likewise, a first x-axis patch 58a and a second x-axis patch 58b can be connected with the patient 26 to create a x-axis (such as an axis that is generally medial-lateral of a patient) with a voltage gradient substantially along the x-axis between the patches 58*a* and 58*d* and a corresponding x-axis current flowing between patches 58*a* and 58*b*. Finally, a first z-axis patch 60*a* and a second z-axis patch 60*b* can be connected with a patient 26 to create a z-axis (such as an axis that is generally anterior-posterior of a patient) with a voltage potential gradient substantially along the z-axis between the patches 60*a* and 60*b* with a corresponding z-axis current flowing between the patches 60*a* and 60*b*. The three axes are generally formed to have an organ or area of interest at the common intersection or origin of each of the axes x, y, z. Accordingly, the axis patches or electrodes 56*a*-60*b* can be positioned on the patient 26 to achieve the selected placement of the axes x, y, z relative to the patient 26. Each of the patches 56*a*-60*b* can be interconnected with the PSU input/output (I/O) box 52, via a wire connection or other appropriate connection at the ports 54.

The current applied between the related patches generates a small or micro-current, which can be about 1 microampere (µA) to about 100 milliamperes (mA), in the patient along the axis between the respective patch pairs. The induced current can be of a different frequency for each of the related patch pairs to allow for distinguishing which axis is being measured. The current induced in the patient 26 will generate a voltage gradient across different portions, such as the heart, that can be measured with a position element. The position element can be an electrode, as discussed in further detail herein. The sensed voltage can be used to identify a position along an axis (whereby each axis can be identified by the particular frequency of the current being measured) to generally determine a position of an electrode along each of the three axes. Although a voltage can be sensed, an impedance can also be calculated or measured to determine a location in a similar manner. It will be understood, that a sensing of voltage will not eliminate other possible measurements for position determination, unless specifically indicated. As discussed further herein, the position of the electrode with respect to each of the three axes can be used as map data to be illustrated on the display device 38. Position elements can be electrodes within the patient and reference electrodes are interconnected with the PSU I/O box 52 such that the signals are processed by high impedance circuitry so as to not load and distort the sensed signals.

In addition, reference patches or electrodes can be interconnected with the patient 26 for reference of guiding or mapping with the instrument relative to the patient 26. The reference electrodes can also be used for reference of position of leads within the patient 26. The reference patches can include a first reference patch 62*a* and a second reference patch 62*b*. The placement of the reference patches 62*a*, 62*b* can be any appropriate position on the patient 26, including those discussed further herein according to various embodiments. For example, the first reference patch 62*a* can be positioned substantially over the xiphoid process on the skin of the patient 26 directly exterior to the xiphoid process of the patient 26. The second reference patch 62*b* can be positioned substantially directly across from the first patch 62*a* on a dorsal surface of the patient 26.

By positioning the reference patch 62*a* at the xiphoid process of the patient 26, the reference patch 62*a* has relatively less motion with respect to the heart than many other locations on the skin of the patient 26. The heart 42 of the patient 26 is substantially static in position relative to the xiphoid process. By positioning the reference patches 62*a,b* at these locations, respiration may be monitored by measuring the relative voltage or impedance difference between the two reference electrodes 62*a,b* using the PSU 36. As discussed herein, impedance or voltage measured between the two reference patches 62*a,b* can be used to determine a respiratory cycle and the portion of the cycle that the patient 26 is in. Also, the reference patches 62*a,b* can be used to assist in monitoring the cardiac cycle in a similar manner. As discussed herein, one or both of the reference electrodes can be used for selected procedures. Accordingly, reference can be made to the dorsal reference electrode 62*b* alone or in addition to the xiphoid reference electrode 62*a*.

The PSU I/O box 52 can be interconnected with the workstation 39, via a connection or data transfer system 68. The data transfer system 68 can include a wire transmission, wireless transmission, or any appropriate transmission. The workstation 39 can receive signals, which can be analog or digital signals, regarding voltages sensed by the reference patches 62*a*, 62*b* and electrodes on the instrument lead 101 (FIG. 3). The signals can be used to determine a relative location of the instrument and to display the determined relative location on the display device 38. The display device 38 can be integral with or separate from the workstation 39. In addition, various interconnected or cooperating processors and/or memory can be provided to process information, each may be a part of the workstation 39 or separate therefrom. The processors can process the signals from the patches 56*a*-60*b* and instrument to determine the position of the instrument, display the determined positions or other data on the display device 38.

The navigation system 20 can further include user input or data input devices such as a keyboard 64, a joystick 65, or a foot pedal 66. Each of the input devices, 64-65 can be interconnected with the workstation 39 or appropriate systems for inputting information or data into the workstation 39. This information or data can include identifying appropriate information, as discussed further herein, such as various components, or anatomic regions.

With continuing reference to FIGS. 1 and 2, with particular reference to FIG. 2, the multiple driving or voltage patches 56*a*-60*b* are used to inject current in the patient to create voltage potentials within the patient 26 that can be sensed by electrodes that are positioned on or within the patient 26. It will be understood that the axis patches 56*a*-60*b* can be positioned on the patient 26 at any appropriate locations, such as the locations described with the LocaLisa™ position sensing unit previously provided by Medtronic, Inc. of Minneapolis, Minn., USA. The PSU I/O box 52, can create voltages and generate a small current along the axes between the related patches. The current generated can include different frequencies along the different x, y, and z axes to distinguish the x, y, and z-axes.

The PSU 36 including the several patches can inject a current into the patient 26. The current that is injected can be a substantially stable current that is not substantially changed over time. If the current is substantially stable then a voltage can be measured with an instrument or reference patch, as discussed herein and above, to be used in determining a location of the instrument or the reference patch relative to the axis on the patient 26. Alternatively, or in addition thereto, an impedance can be determined based upon a measured current that is injected in the patient and the measured voltage with the instrument reference patch. The impedance can, therefore, be used to determine a location of the instrument or the referenced patch. Accordingly, it will be understood that the position of an electrode, such as of an instrument, can be determined based upon a relationship of Ohms Law by determining an impedance or measuring voltage within the patient 26 or any appropriate volume.

With additional reference to FIG. 3, the instrument can include a lead electrode 100 that is a part of a lead 101 that is able to sense the voltage generated within the patient 26 due to the patches 56a-60b positioned on the patient 26. The sensed voltage can be used to calculate an impedance of the tissue in the patient 26 based upon the voltage potential gradient generated between the respective pairs of patches and the corresponding current. Generally, the current is carried due to an electrolyte in the patient 26, such as blood, interstitial fluid, etc. within a heart 42 and body of the patient 26.

Reference Electrodes

As discussed further here, the calculated impedance or sensed voltage can be used to determine a location of the electrode of the instrument relative to a selected reference, such as reference patch 62a or 62b. The reference patches 62a, 62b can be positioned at any appropriate position on the patient 26. As discussed above, the first reference patch 62a can be positioned substantially over the xiphoid process of the patient 26. The positioning of the first reference patch 62a over the xiphoid process of the patient 26 can limit movement of the reference patch 62a due to respiration or cardiac movement. The second reference patch 62b can be positioned substantially directly across the thickness of the patient 26 on a dorsal side of the patient 26 from the first reference patch 62b. The reference patches 62a, 62b can also be used for repeat or multiple procedures at different times.

The two reference patches 62a, 62b can be on the same horizontal plane. The horizontal plane is perpendicular to the coronal or median planes of an anatomy. The second reference patch 62b can also be substantially fixed relative to the patient 26, at least in part because it is positioned on the dorsal side of the patient 26 and the patient is supine for the procedure of lead implantation.

Reference patches can also be used to avoid errors caused by voltage drop of the axis electrode patches through which current flows into the patient 26 at the tissue patch interface. Patches driven with current have a voltage drop across the electrode tissue interface. Using raw unreferenced voltage introduces measurement error which is eliminated by use of a reference. The reference electrodes can be used to measure the voltage drop.

Lead Instrument

With reference to FIG. 3, the lead 101 is illustrated that can also be used as the instrument. The lead 101 can be any appropriate lead such as the model 5076 sold by Medtronic, Inc. of Minneapolis, Minn., USA. The lead 101 can be used as part of an implantable medical device 70, which can have any appropriate numbers of connections for leads, such as a first 72 and a second 74 connection. The position of the lead 101, can be determined and displayed on the display device 38, as discussed further herein. The lead 101 can include an external sheath or covering 102 that substantially insulates an interior of the lead 101 from an external environment, such as an anatomical portion. The lead 101 can include a conductor 103 and the retractable helix electrode 100. The electrode 100 can be used with the PSU 36 to determine the location of the electrode 100.

As discussed herein, the determined position of the lead 101 can be illustrated on the display device 38. It will also be understood, the lead 101 may include more than the implantable electrode 100. The lead 101 may include at least a second electrode, such as a ring electrode. A voltage can also be sensed by any of the electrodes and also be used for determining a position of the lead 101 or a portion thereof.

Synchrony Determination

As briefly discussed above, axis electrodes 56a-60b can be positioned on the patient 26 for injecting currents into the patient 26 to determine a location of the electrode 100 positioned within the patient 26. The electrode 100 can include or be part of the lead 101 that is implanted in the patient 26 that can later be connected to the implanted medical device (not illustrated) such as a cardiac pacemaker, a defibrillator, a cardioverter, or other appropriate devices.

As illustrated in FIG. 2 more than one lead can be positioned in the patient 26. The first electrode 100 can be positioned in a right ventricle 82 of the heart 42 of the patient 26 and the second electrode 104 of the second lead 105 can be positioned in a left ventricle 84 of the patient 26. A septal wall 86 of the heart 42 can separate the two ventricles, 82, 84. The second electrode 104 can be the electrode of the second lead 105 interconnected with the heart 42 of the patient 26, for various procedures such as implantation of an implantable medical device 70 (FIG. 3) including a CRT pacemaker or defibrillator.

The leads 101, 105 can be positioned in the heart 42 in a manner understood by one skilled in the art, and schematically illustrated in FIG. 2. Generally, a CRT aims to place leads electrodes diametrically across the left ventricle. The first lead 101 can be passed through the superior vena cava into the right ventricle 82 and the first electrode against an interventricular septum in the heart 42. The second lead 105 can follow the route through a coronary sinus, a great cardiac vein, and down to a tributary that provides a position in apposition to the lead electrode 100. The second lead electrode 104 can then be placed in apposition to the first lead electrode 100.

Accordingly, it will be understood that the first and second leads 101, 105 can be connected to the PSU system 36 for determining the position of both of the electrodes 100, 104 as discussed further herein. It will be further understood, also, that any appropriate number of leads can be positioned within the patient 26 for measurements as discussed further herein. For example, additional leads can be positioned within the atria of the heart 42 or in other portions of the patient 26. It will be further understood that the leads are electrodes, and may also be referred to as such. Moreover, any electrode can be connected with the PSU 36.

The position of the electrodes positioned within the heart 42, such as the first electrode 100 and the second electrode 104 (which can be positioned in the right and left ventricles, respectively) can be tracked with the PSU 36. When positioned, the electrodes 100, 104 can be substantially fixed relative to a wall portion of the heart 42. The PSU 36 can include a processor or communicate with a processor of the workstation 39, or any appropriate processor, to execute instructions to determine locations of the electrodes as the heart 42 of the patient 26 beats. As the heart 42 of the patient 26 beats, the two electrodes 100, 104 can move relative to one another and relative to various points on the skeletal-muscular structure of the patient. Motion of the electrodes as secured within a heart wall can serve as a surrogate for measurement of the relevant regions of the heart wall. Assuming that the two leads 100, 104 are fixed within the heart 42, their motion can be determined to be the motion of the heart 42. These positions can be used to measure RV 82 and LV 84 motion and dimensions.

Figure 4:
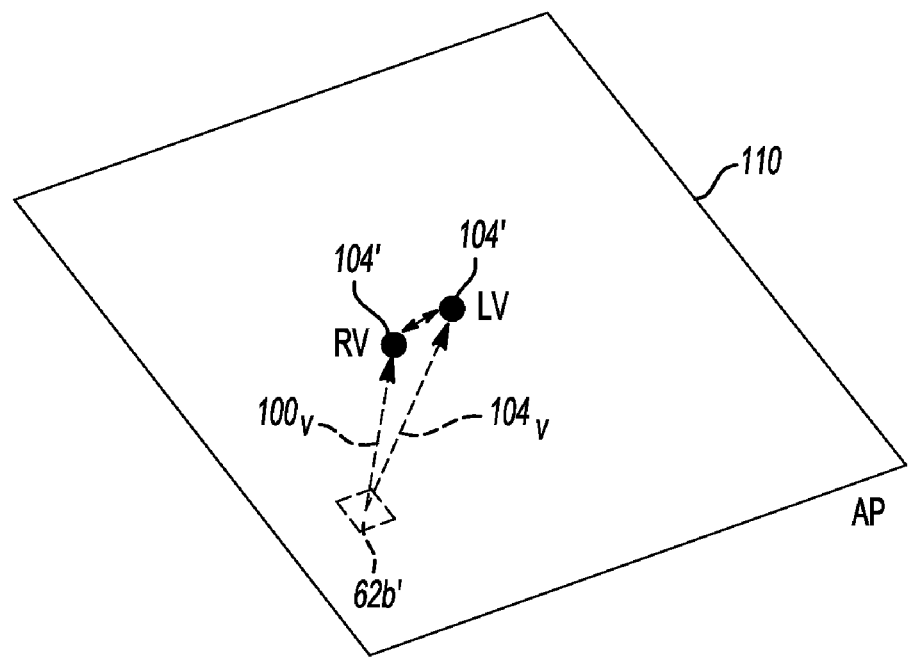
FIG. 4 is a schematic view of an illustration of a lead position projected onto a plane.

The processor or processing system can illustrate the motion of the leads 100, 104 over time as projected on a selected plane. For example, an anterior to posterior view or plane 110, as illustrated in FIG. 4, can be used to illustrate the motion of the two electrodes 100, 104 over time. The AP plane 110 view can be understood to be the same view of the patient 26 as illustrated in FIG. 2 that is an anterior or front view of the patient 26 with the patient's right side displayed to the left of FIG. 4.

As illustrated schematically in FIG. 4, the electrodes 100, 104 can be illustrated or represented by icons 100', 104' projected onto a selected plane, such as the AP plane 110, which can be an anterior to posterior plane relative to the patient 26. Because the two leads 100, 104 are fixed to the patient 26 in the heart 42, they will move relative to one another over time as the heart 42 beats. The movement of the electrodes 100, 104 can be determined relative to a reference such as the reference electrode 62b which is illustrated schematically as in FIG. 4.

A displacement vector 100v can be determined between the reference electrode 62b and the right ventricle electrode 100 and a displacement vector 104v determined between the reference electrode 62b and the left ventricle electrode 104. The displacement vectors 100v, 104v of the two electrodes 100, 104 can be determined by tracking the position of the electrodes 100, 104 with the tracking system, as discussed above. It will be understood that determining the position of the electrodes 100, 104 can be determined as discussed above and will not be discussed in detail here.

Figure 5:
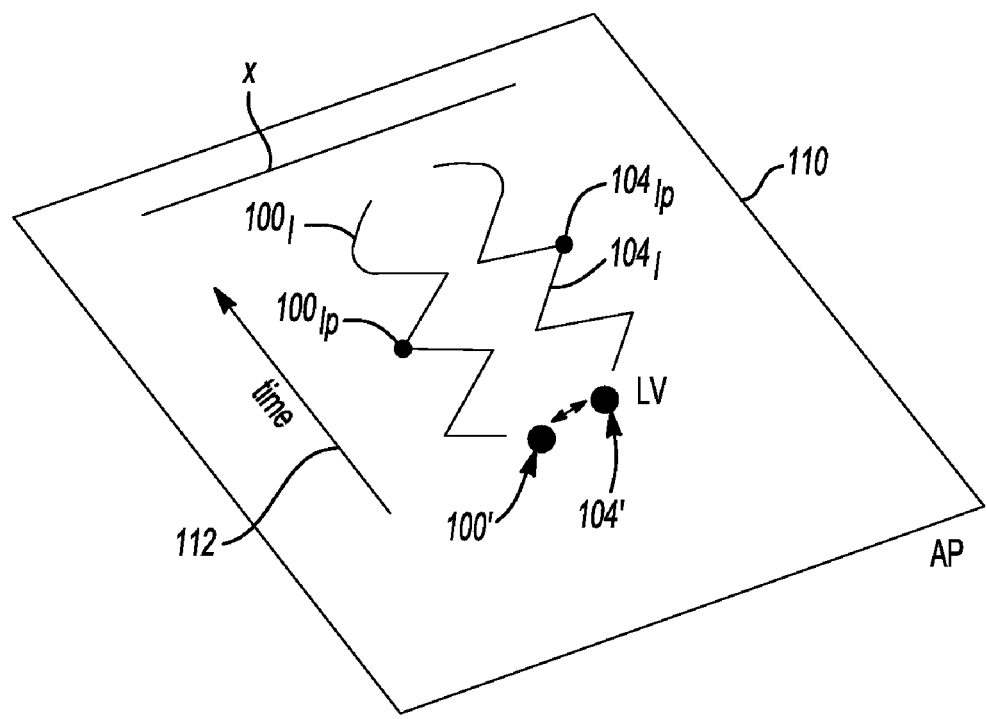
FIG. 5 is a schematic view of a position of the lead projected on a plane over time.

With the displacement vectors of the two electrodes 100, 104 determined, a projection of a unit vector can be made relative to the AP plane 110 to illustrate the relative position of the electrodes over time, as schematically illustrated in FIG. 5. In particular, as schematically illustrated in FIG. 5, the traces 100I, 104I can be shown relative to a time axis 112 on the AP plane 110. Essentially, the electrodes 100, 104 remain fixed in place, but their displacement can be represented as the traces on the plane 110 as a trend line by imagining that the plane is moved over time and a line is drawn from the points 100', 104' representing the electrodes 100, 104. Alternatively, the points 100', 104' can be imagined to be moved over the plane 110 over time to firm the traces 100I, 104I. As the plane is moved and the positions of the electrodes 100, 104 are determined, they can be illustrated relative to one another as traces 100I, 104I respectively.

The trace information can be used to determine whether synchrony or dysynchrony is present within the heart 42. For example, as illustrated schematically in FIG. 5, if the traces 100I, 104I are substantially mirror images or oppose one another, then synchrony can be determined to be occurring. However, if the traces 100I, 104I are not opposed to one another or are somewhat in opposition but with other than being completely out of phase then dysynchrony can be determined. Pacing adjustment can then be made to attempt to achieve synchrony or repositioning of one or more of the electrodes 100, 104 can be performed to attempt to achieve synchrony. Synchrony can be defined as discussed herein.

Figure 6:
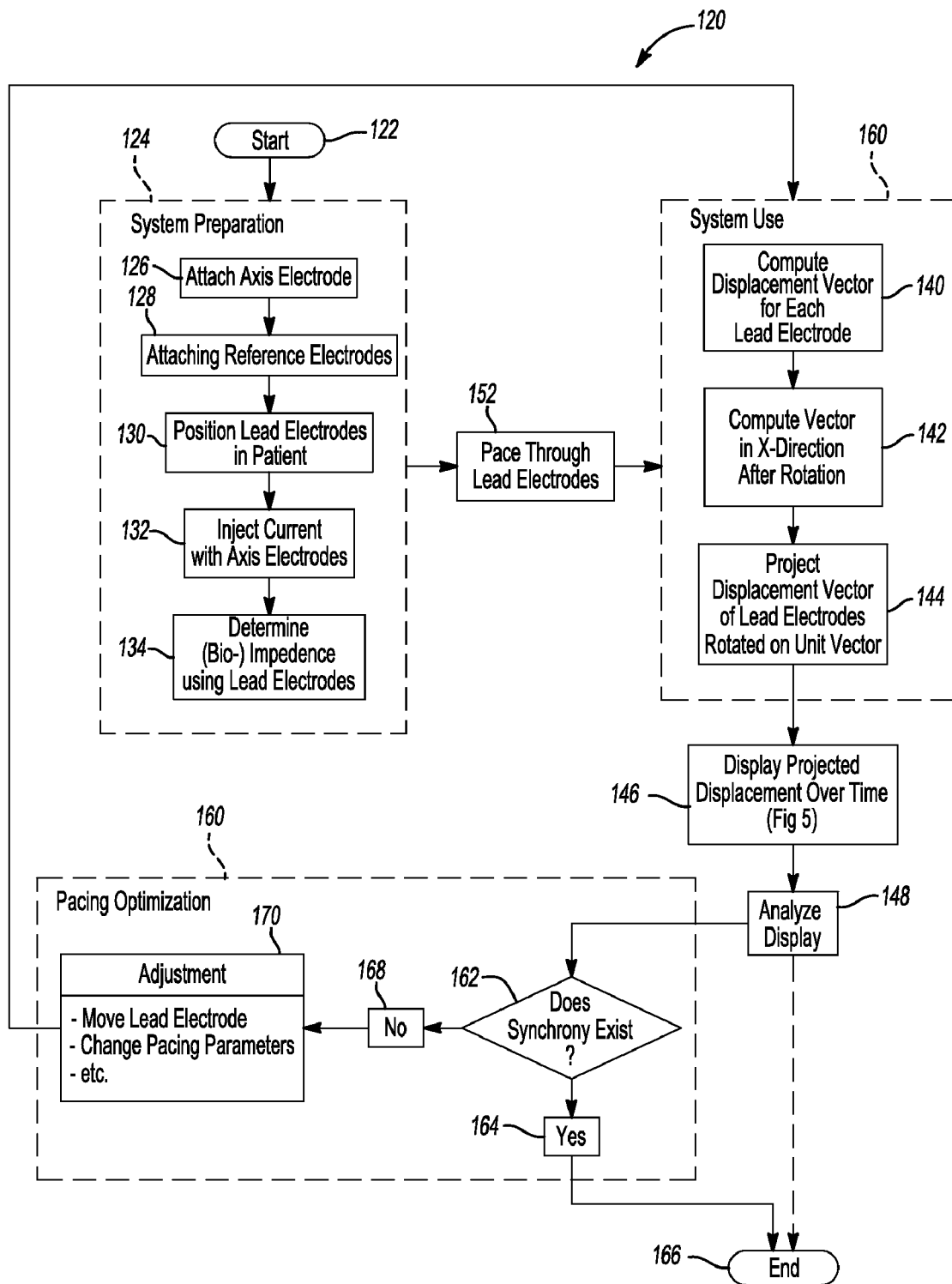
FIG. 6 is a flowchart of a method for performing a procedure.

To project the traces 100I, 104I onto the AP plane 110, the information of movement or displacement of the electrodes with the EP tracking system 36 can be determined according to a method illustrated in the flowchart 120 in FIG. 6. The method illustrated in the flowchart 120 in FIG. 6 can begin in start block 122. Optionally, in block 124, the system can be prepared for use, such as being connected to the patient 26, for clarity of the current discussion, it will be understood that it will not be required as a part of the method for the flowchart 120.

System preparation can include connecting an appropriate number of injection or axis electrodes to the patient 26 in block 126. A connection of an appropriate number of reference electrodes can occur in block 128. As discussed further herein, an appropriate number of axis electrodes can include 4 axis electrodes, which can be two pair of axis electrodes to generate two axes if rotation around a minimal number of axes is required. Additionally, only a single reference electrode may be used to determine the displacement of the electrodes positioned within the patient 26. Accordingly, although the PSU system 36 as illustrated above can include six axis electrodes and two reference electrodes, the system 36 can also be used including only four axis electrodes and one reference electrode. The lead electrodes can be positioned in the patient 26 in block 130. Current can then be injected with the axis electrodes in block 132. The lead electrodes can then be used to determine a bioimpedance in block 134.

After the system preparation in optional block 124, the displacement of the vector for each of the lead electrodes can be computed in block 140. The computed displacement vector for each of the lead electrodes can be calculated or determined as discussed above. The position of the lead electrodes can move relative to the reference electrodes 62a, 62b (while the discussion herein will relate to one of the reference electrodes 62b, it will be understood that the discussion can also relate to either or both of the reference electrodes 62a,b). The displacement vector for the lead electrodes relative to the reference electrodes can be computed based upon a position or movement of the lead electrodes relative to the reference electrode using the PSU 36. The lead electrodes can be connected to the controller 52, as illustrated in FIG. 2. The bioimpedance determined using the lead electrodes 100, 104 can be used to determine the respective displacement relative to the reference electrode 62b using the tracking system 36, as discussed above.

Once the displacement vectors are determined for each of the lead electrodes 100, 104, a projection of the vectors can be illustrated on the AP plane 110, as schematically illustrated in FIGS. 4 and 5. The unit vector can be along the x-axis. The x-axis can be illustrated on the AP plane 110. The unit vector can be rotated around coordinates of the multi-dimensional coordinates determined with the PSU 36 based upon the multiple axes generated relative to the patient 26 with the axis electrodes connected to the patient 26 in the system preparation block 126.

Generally, the displacement vector can be illustrated as a vector along a unit vector. In other words, a unit vector can be selected and selected displacement vectors (e.g. of the two electrodes 100, 104) can be projected onto the unit vector. It will be understood that any appropriate number of axes can be determined for the displacement vectors, and the resultant displacement vectors can be projected onto the unit vector to understand the changes or trends over time.

Computing the displacement vector $\vec{D}(t)$ can include subtracting an initial or first location vector $\vec{P}(t_o)$ from a current location vector $\vec{P}(t)$ as represented in FORMULA 1:

$$\vec{D}(t) = \vec{P}(t) - \vec{P}(t_o)$$

where $\vec{P}(t)$, is determined by the PSU 36. The location vectors can be for the respective electrodes 100, 104. Accordingly, a displacement vector can be computed for both of the electrodes 100, 104 to allow for the projection of a location of both of the electrodes 100, 104 as represented in FIG. 5, over time. Further, $\vec{P}(t_o)$ represents the starting time of the processed signal or the time for originally processing the signal by the PSU 36. The displacement vector for either of the electrodes 100, 104 can be understood to be a current location relative to an initial location at $t_o$. As time passes, the position of the electrodes 100, 104 move relative to the initial position and can be projected onto the plane 110 as illustrated in FIG. 5.

A unit vector can be computed for use in projecting the displacements on the plane 110, as illustrated in FIG. 5.

Computing the unit vector can be performed in block 142 starting with an initial unit vector and a first axis which is normal to the initial unit vector. The initial unit vector is first rotated around the first axis by angle θ. A second axis is defined as normal to the plane including the first axis and the first rotated unit vector. The first rotated unit vector is then rotated around the second axis by angle φ. The unit vector $\vec{N}$ is then defined for the case where the initial vector is in the x-axis direction by FORMULA 2:

$$\vec{N} = (\cos(\phi)\cos(\theta), \cos(\phi)\sin(\theta), \sin(\phi)).$$

The displacement vector according to FORMULA 1 can then be projected to the rotated unit vector $\vec{N}$ by computing the inner product of the two vectors according to FORMULA 3:

$$<\vec{D}(t), \vec{N}> = D_x N_x + D_y N_y + D_z N_z = \cos(\phi)\cos(\theta) D_x + \cos(\phi)\sin(\theta) D_y + \sin(\phi) D_z$$

in block 144, where $D_x$, $D_y$, and $D_z$ are the displacement vectors according to FORMULA 1 in each of the x-, y-, and z-axes.

After projecting the displacement vectors on the rotated unit vector a display of the projected displacement over time can be performed in block 146. As discussed above, the displayed projected displacement can be done to the display device 38 that displays the position of the lead electrodes 100, 104 as icons or points 100', 104' projected onto the plane 110. The display can then be analyzed in block 148, as discussed above, regarding synchrony of movement of the heart 42. It will be further understood that the position or displacement of the electrodes need not be displayed on a viewable monitor but can be analyzed by a processor system to determine synchrony or dysynchrony of the heart 42.

After the system is prepared in block 124, as discussed above which is not a requirement of the method of determining synchrony or dysynchrony, however, pacing through the lead electrodes in block 152 can be performed. Pacing through the lead electrodes in block 152 can occur prior to using the system to project displacement vectors of the lead electrodes onto the selected plane 110. It will be understood that the displacement of the lead electrodes can be projected with or without pacing, therefore pacing in block 152 is not necessary. As discussed in the present disclosure, according to various embodiments, using the method and system disclosed can be used to determine whether the selected pacing parameters achieve synchrony within the heart 42. Accordingly, pacing through the lead electrodes in block 152 prior to a system use block 150 can occur.

It will be further understood that a processor system can execute instructions stored in a memory system to perform the functions in blocks 140, 142, and 144. An appropriate processor system can also be referred to as a position processor system illustrated by block 150 in FIG. 6. The position processor system or blocks can process the position information determined by the PSU 36 to compute the displacement vectors and project the displacement vectors onto the rotated unit vector. The processor system can be incorporated into the PSU 36, the workstation 39, or be separate from both. In addition, processing functions can be shared amongst the various systems. Similarly, the memory system can be associated with one or all systems. An output can then include displaying the positions projected onto a display device for viewing by a user or output to a separate algorithm or processing system for analyzing the position or displacement information to determine synchrony or other information regarding position of the electrodes within the heart 42.

Figure 7:
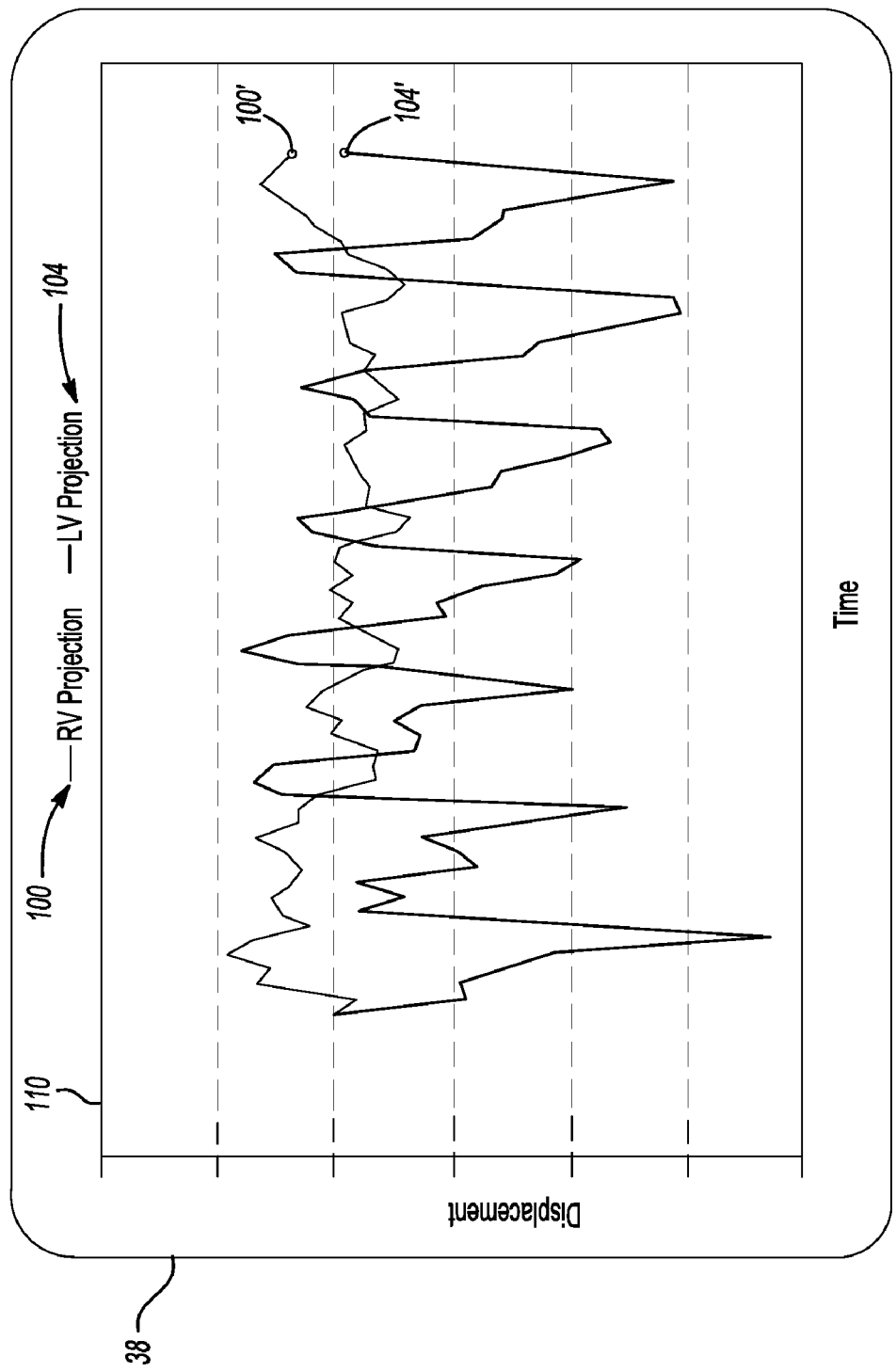
FIG. 7 is a detailed view of an exemplary tracked location of lead points projected on a plane over time.

Analyzing the position data, as schematically illustrated in FIG. 5 and exemplarily illustrated in FIG. 7 can be used to optimize positioning of the leads 100, 104 in the heart 42. FIG. 7 illustrates exemplary traces obtained after tracking and projecting the position of two electrodes in a porcine heart. The projected positions of the leads are illustrated as trend line or the traces 100I, 104I. The determined position is shown over time (the long axis in FIG. 7). The illustrated traces 100I, 104I can be used to determine or analyze synchrony.

Because the leads including the lead electrodes 100, 104 are connected to the PSU 36, the position of the electrodes 100, 104 can be determined prior to a final implantation of the IMD into the patient 26. Accordingly, the analysis can be used to determine the appropriate pacing of the heart 42 or whether the position of the electrodes 100, 104 is appropriate. For example, the position of the electrodes 100, 104 can be determined over time while applying selected pacing characteristics. For example, a pacing analyzer 53 (FIG. 2) can be connected to the electrodes 100, 104 through the PSU 36. The selected pacing signal can then be transmitted through the leads to the lead electrodes 100, 104 to pace the heart 42 at a selected manner, as in block 152. The position of the electrodes 100, 104 can be tracked with the PSU 36 over time during any appropriate selected pacing characteristics.

As discussed above, pacing can be performed with the lead electrodes 100, 104 according to selected pacing parameters in block 152 and the effect of this pacing can be analyzed in block 148. The pacing can be analyzed according to a synchrony determining process or loop in block 160. The process loop in block 160 can include a determination of whether synchrony exists in block 162. If synchrony exists, then the YES block 164 can be followed to the end block 166 in the flowchart 120.

Synchrony can be identified by the user 32 or by executing instructions with the processor system to determine synchrony. Synchrony can be quantified either in time (milliseconds) or phase angle (degrees). A generally accepted standard guideline for indicating patients for CRT is a QRS width of greater than 120 ms. Generally, synchrony can be determined to exist if the opposition of the traces, as illustrated in FIG. 5 or 7, are within about 40 milliseconds of one another. That is, if a determined position of the first electrode 100 is at a peak 100Ip within about 40 milliseconds of when a peak 104Ip of the second electrode 104 is traced, then synchrony exists, and the same for the valleys. A phase difference of about 30 degrees can also be used to define synchrony. It will be understood that perfect synchrony (i.e. no time difference between opposed peaks and values) may not exist, but the user 32 can determine that an optimal or appropriate synchrony exists based on the analysis in block 148. In addition, as illustrated in FIG. 7, the peaks and valleys may not be exceptionally sharp and may include other noise or small signals, accordingly the variance disclosed above can be used in determining synchrony.

If a determination that synchrony does not exist in block 162, then the NO block 168 can be followed to an adjustment block 170. The adjustment block 170 can include various adjustments. Exemplarily adjustments can include moving the electrodes 100, 104, either or both, to new locations. Alternative adjustments can include adjusting the pacing parameters, such as pulse width, power, voltage, and the like. Other appropriate adjustments can also be used, as those generally skilled in the art will understand. Once adjustments occur in block 170, the system use block 150 can again be accessed to determine and project the displacements of the lead electrodes onto a selected unit vector or plane 110. Once the analysis occurs again in block 148 after the adjustment in block 170, the determination of whether synchrony exists in block 162 can further be queried. If synchrony is found to exist, then the YES block 164 can be followed to the end block 166.

Accordingly, the method and flowchart 120 can be used to optimize or select appropriate locations and pacing parameters for achieving synchrony or a selected heart motion in the patient 26. It will be understood that the use of the pacing or synchrony optimization in block 160 can be iterated through several times until the appropriate or optimized synchrony or heart motion is achieved.

As discussed above, synchrony can be determined when the traces have appropriately opposed peaks. Moreover, the pacing analyzer 53 can be used to change the pacing parameters such as the time between stimulating the left and the right ventricles 82, 84 or the time between atrial depolarization and stimulating each of the right and left ventricles 82, 84 prior to implanting the implantable medical device. The user 32 can view the display or the analysis to determine if the traces are becoming more or less synchronous based on the changing pacing parameters. Thus, the user 32 alone or in addition to the processor can analyze interpret the analysis of block 148 to determine how the pacing parameters may be changed to achieve synchrony or optimal pacing.

It will be understood that the leads 100, 104 can be any appropriate leads that are able to be positioned in the heart 42. Further, however, the leads 100, 104 can be the lead electrodes that will be implanted with an IMD after an appropriate position of the lead electrodes 100, 104 is determined. Therefore, the PSU 36 can be used to track the location of the leads 100, 104 and they can be maintained in the tracked location once an appropriate synchrony or heart motion is achieved. This allows the leads 100, 104 to be analyzed in their final implanted position without repositioning from a selected location. For example, it does not require or necessitate the removal of a tracked element before the implantation of an implanted lead electrode at the exact same location.

In addition, because the PSU 36 can work with the electrodes of the lead electrodes 100, 104, no additional tracking devices need be added to the leads 101, 105. Appropriate and accepted implantable leads can be connected with the PSU I/O 52 and used with the PSU 36 to determined positions of the leads 100, 104. As discussed above, the reference electrodes 62a,b of the PSU 36 can be used to determined displacement of the leads 100, 104 relative to the reference electrode 62a,b.

The tracked position of the lead electrodes 100, 104 allows for tracking the final position of the lead electrodes 100, 104 in an efficient manner. This also allows for the determined position or tracked position of the lead electrode to be tracked in a generally inaccessible area, such as the left ventricle of the heart 42. The leads 100, 104 can then be maintained in the exact location used during the analysis of block 148 by tracking the location of the lead 100, 104.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A method of determining movement of a portion of a subject, comprising:
   positioning a first implantable lead having a first implantable electrode into a structure of the subject and positioning the first implantable electrode at a first location;
   positioning a second implantable lead having a second implantable electrode into a structure of the subject and positioning the second implantable electrode at a second location;
   positioning a third electrode on or in the subject;
   injecting at least two axes of current into a volume of the subject;
   determining a first impedance using the positioned first implantable electrode and the third electrode;
   determining a second impedance using the positioned second implantable electrode and the third electrode;
   executing instructions with a processor external to the subject to determine a plurality of sequential first positions of the first implantable electrode and a plurality of sequential second positions of the second implantable electrode based on the determined first impedance and the determined second impedance using the positioned first implantable electrode, the positioned second implantable electrode, and the third electrode;
   calculating a unit vector;
   projecting a first displacement vector representing motion of the positioned first implantable electrode onto the unit vector and a second displacement vector representing motion of the positioned second implantable electrode onto the unit vector;
   illustrating a plurality of projected positions on a plane of the subject over time; and
   determining motion of the structure of the subject based on the determined plurality of sequential first positions of the first implantable electrode and the plurality of sequential second positions of the second implantable electrode.

2. The method of claim 1, wherein selecting the unit vector includes rotating an initial unit vector around one of two injected axes relative to the selected unit vector.

3. The method of claim 2, further comprising:
   injecting three axes into the volume of the subject;
   wherein selecting the unit vector includes rotating the initial unit vector around two of the three injected axes relative to the selected unit vector.

4. The method of claim 1, wherein rotating a component of a first vector and a second vector includes executing instructions with the processor to mathematically compute the rotations.

5. The method of claim 1, wherein illustrating the plurality of positions on the plane over time includes illustrating a line.

6. The method of claim 1, further comprising:
   implanting an implantable medical device into the subject to at least one of cardiovert the heart of the subject, pace the heart of the subject, defibrillate the heart of the subject or combinations thereof.

7. The method of claim 6, further comprising:
   implanting the first implantable electrode and the second implantable electrode; and
   connecting the first implantable electrode and the second implantable electrode to the implantable medical device.

8. The method of claim 1, further comprising:
   selecting a pacing parameter;
   pacing the structure of the subject with the selected pacing parameter; and determining whether synchrony exists in the structure with the selected pacing parameter.

9. The method of claim 8, further comprising:
when dysynchrony exists, alter the pacing parameter to achieve synchrony prior to implanting an implantable medical device.

10. The method of claim 9, further comprising:
when synchrony exists, maintaining the first implantable electrode and the second implantable electrode at the first and second respective positions;
implanting an implantable medical device into the subject; and
connecting the first lead and the second lead to the implantable medical device.

11. The method of claim 8, further comprising:
when dysynchrony exists, moving at least one of the first implantable electrode or the second implantable electrode to a third position different from the first or second position in the structure of the subject.

12. A method of determining movement of a portion of a subject, comprising:
positioning a first implantable lead having a first implantable electrode into a right heart portion of the subject and positioning the first implantable electrode at a first location in the right heart portion;
positioning a second implantable lead having a second implantable electrode into a left heart portion of the subject and positioning the second implantable electrode at a second location in the left heart portion;
selecting first pacing parameters;
pacing the heart of the subject according to the selected first pacing parameters with the first implantable electrode and the second implantable electrode;
tracking, relative to a reference portion, the location of the first implantable electrode in the right heart portion and the second implantable electrode in the left heart portion with an external tracking system;
executing instructions with a processor external to the subject to determine a plurality of sequential first positions of the first implantable electrode and a plurality of sequential second positions of the second implantable electrode based on a determined impedance using both the positioned first implantable electrode and the positioned second implantable electrode;
calculating a selected plane of the subject, the selected plane having a unit vector;
projecting the plurality of first sequential positions and the plurality of second sequential positions onto the unit vector of the selected plane of the subject; and
determining whether synchrony of the heart of the subject exists based on the projected plurality of first sequential positions and plurality of second sequential positions;
wherein determining existence of synchrony of the heart includes observing the plurality of positions during pacing the heart.

13. The method of claim 12, further comprising:
injecting at least two axes of current into a volume of the subject with the external tracking system;
wherein tracking the location of the first implantable electrode in the right heart portion and the second implantable electrode in the left heart portion with an external tracking system includes determining an impedance using the positioned first implantable electrode and the positioned second implantable electrode relative to a third reference electrode.

14. The method of claim 13, further comprising:
displaying on a display device the projection;
wherein the projection can include two lines illustrating the plurality of first and second sequential positions;
wherein synchrony is determined by observing an existence of opposition of the relative positions of the projected plurality of first sequential positions and the plurality of second sequential positions.

15. The method of claim 14, wherein the lines illustrate a first trace of the plurality of first sequential positions of the first implantable electrode and a second trace of the plurality of second sequential positions of the second implantable electrode over time relative to a selected unit vector.

16. The method of claim 15, wherein the plurality of first and second sequential positions are projected positions of the respective first and second implantable electrodes relative to the subject and include projection on the selected unit vector.

17. The method of claim 16, further comprising:
moving at least one of the first implantable electrode or the second implantable electrode to achieve synchrony; and,
determining the existence of synchrony of the heart of the subject after moving the at least one of the first implantable electrode or the second implantable electrode.

18. The method of claim 13, further comprising:
selecting alternative pacing parameters;
wherein determining the existence of synchrony includes determining the existence of synchrony after applying the alternative pacing parameters.

19. The method of claim 13, wherein executing instructions with a processor external to the subject to determine a plurality of first sequential positions of the first implantable electrode and a plurality of second sequential positions of the second implantable electrode, further comprises:
wherein positioning a reference includes positioning a reference electrode relative to the subject;
determining a first initial position vector of the first implantable electrode and a second initial position vector of the second implantable electrode relative to the reference electrode;
determining subsequent first position vectors for the first implantable electrode and subsequent second position vectors for the second implantable electrode relative to the reference electrode; and
determining the difference between the initial and the subsequent position vectors for each of the first and second electrode.

20. The method of claim 13, further comprising:
when synchrony is determined to exist, maintaining the first implantable electrode at the first position and the second implantable electrode at the second position;
connecting the first lead and the second lead to an implantable medical device; and
implanting the implantable medical device into the subject.

21. The method of claim 12, wherein tracking the location of the first implantable electrode in the right heart portion and the second implantable electrode in the left heart portion with an external tracking system includes:
tracking, relative to an electromagnetic reference position, a first location of a first electromagnetic tracking device associated with the first implantable electrode and a second location of a second electromagnetic tracking device associated with the second implantable electrode.

22. The method of claim 12, wherein tracking the location of the first implantable electrode in the right heart portion and the second implantable electrode in the left heart portion with an external tracking system includes:

positioning an excitable reference member at a position relative to the heart;

tracking a first location of a first excitable marker tracking device associated with the first implantable electrode relative to the positioned excitable reference member; and tracking a second location of a second electromagnetic tracking device associated with the second implantable electrode relative to the positioned excitable reference member.

23. A system to determine motion of a structure in a subject, the system having a first lead electrode operable to be implanted and connected to an implantable medical device, a second lead electrode operable to be implanted and connected to the implantable medical device, and at least two pair of axis electrodes operable to inject two axes of current into the subject, the system further comprising:

a processor operable to execute instructions to:
determine a position of the first electrode and the second electrode based on a determined impedance with the first electrode and the second electrode;
selecting a unit vector;
project the determined positions of the first electrode and the second electrode onto the selected unit vector; and
determine a trend of positions over time of the first electrode and the second electrode for illustration relative to the selected unit vector; and a display device to display the determined trend of positions on the selected unit vector over time including a first icon representing a trace of positions of the first electrode over time and a second icon representing a trace of positions of the second electrode over time;

wherein the first icon and the second icon are operable to be viewed to determine synchrony of movement of the structure in the subject.

24. The system of claim 23, further comprising:
the first lead electrode having a first lead extending therefrom;
the second lead electrode having a second lead extending from;
an implantable medical device having a first connection to connect to the first lead and a second connection to connect to the second lead;
a third electrode for reference relative to the first lead electrode and the second lead electrode;
wherein the implantable medical device is operable to inject a current into the structure of the subject through the first and second lead electrodes.

25. The system of claim 24, further comprising:
a pacing analyzer operable to apply pacing parameters to the structure with the first lead electrode and the second lead electrode prior to connection to the implantable medical device.

* * * * *